US00PP26181P3

(12) United States Plant Patent
Nir

(10) Patent No.: US PP26,181 P3
(45) Date of Patent: Dec. 1, 2015

(54) ***CHAMELAUCIUM* PLANT NAMED 'TITAN'**

(50) Latin Name: *Chamelaucium uncinatum*
Varietal Denomination: TITAN

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 129 days.

(21) Appl. No.: 13/987,630

(22) Filed: Aug. 16, 2013

(65) Prior Publication Data

US 2015/0052648 P1 Feb. 19, 2015

(51) Int. Cl.
*A01H 5/02* (2006.01)

(52) U.S. Cl.
USPC ..... Plt./229

(58) Field of Classification Search
USPC ..... Plt./229
See application file for complete search history.

*Primary Examiner* — Keith O. Robinson
(74) *Attorney, Agent, or Firm* — Cassandra Bright

(57) ABSTRACT

A new and distinct *Chamelaucium* cultivar named 'TITAN' is disclosed, characterized by unique large, pale pink flowers and large quantity of buds and flowers,. The new variety is a *Chamelaucium*, normally producing cut flower stems, or as a garden or container plant.

1 Drawing Sheet

Latin name of the genus and species: *Chamelaucium uncinatum.*

Variety denomination: 'TITAN'.

BACKGROUND OF THE INVENTION

The new *Chamelaucium* cultivar is a product of a planned breeding program conducted by the inventor, Nitzan Nir, in Kfar Hess, Israel. The objective of the breeding program was to produce new *Chamelaucium* varieties for ornamental commercial applications. The new variety is a product of cross-breeding that occurred during 2007, at a commercial nursery in Kfar Hess, Israel.

The seed parent is the unpatented, variety *Chamelaucium* 'M.B. Orchid'. The pollen parent is the unpatented, variety *Chamelaucium* 'Hot Pink'. The new variety was discovered in March of 2008 by the inventor in a group of seedlings resulting from the 2007 crossing, in a commercial nursery in Kfar Hess, Israel.

Asexual reproduction of the new cultivar has been performed by vegetative cuttings. This was first performed at a commercial nursery in Kfar Hess, Israel in May of 2008 and has shown that the unique features of this cultivar are stable and reproduced true to type in five successive generations.

SUMMARY OF THE INVENTION

The cultivar 'TITAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TITAN'. These characteristics in combination distinguish 'TITAN' as a new and distinct *Chamelaucium* cultivar:

1. Unique pale pink flower color.
2. Large quantity of buds and flowers
3. Large flower size.

PARENT COMPARISON

Plants of the new cultivar 'TITAN' are similar to plants of the seed parent, *Chamelaucium* 'M.B. Orchid' in most horticultural characteristics, however, plants of the new cultivar 'TITAN' produce a different flower size, more buds and flowers, and have a different branch structure and date of bloom than the seed parent.

Plants of the new cultivar 'TITAN' are similar to plants of the pollen parent; *Chamelaucium* 'Hot Pink' in most horticultural characteristics, however, plants of the new cultivar 'TITAN' produce a different flower size, more buds and flowers, different branch structure and date of bloom than the pollen parent.

COMMERCIAL COMPARISON

'TITAN' can be compared to the unpatented commercial variety *Chamelaucium* 'M.B. Wendy', Plants of 'TITAN' are similar to plants of 'M.B. Wendy' in most horticultural characteristics, however, plants of 'TITAN' produce a different date of blooming, amount of buds/flowers and branch structure than the comparator.

'TITAN' can be compared to the commercial variety *Chamelaucium* 'Umbrella' U.S. Plant patent application Ser. No. 13/986,493. Plants of 'TITAN' are similar to plants of 'Umbrella' in most horticultural characteristics, however, plants of 'TITAN' produce a different branch structure and bloom at a different date than the comparator.

BRIEF DESCRIPTION OF THE PHOTOGRAPH

The accompanying photograph in FIG. 1 illustrates in full color a close up of typical flowers and foliage of 'TITAN'. The age of the photographed variety is approximately 7 months. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'TITAN' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types. Chemical treatments included general fungicides and insecticides.

Botanical classification: *Chamelaucium uncinatum* 'TITAN'.

PROPAGATION

Time to produce a rooted plantlet: 30 to 60 days at approximately 24° C.

Root description: Fibrous, colored near Grey-Brown 199C and 199D.

PLANT

Age of plant described: 2 months from a rooted cutting.
Growth habit: Upright.
Pot size of plant described: 2 liter pot.
Height: 200 cm to top of foliage. 199 cm to top of flowers.
Plant spread: 80 cm.
Growth rate: Rapid.
Branching characteristics:
- *Length of primary lateral branches.*—60 cm to 180 cm.
- *Diameter of lateral branches.*—0.4 cm.
- *Quantity of primary lateral branches.*—120-150.

Characteristics of primary lateral branches:
- *Form.*—Round.
- *Diameter.*—0.5 cm.
- *Color.*—Near RHS Yellow-Green 147A.
- *Texture.*—Smooth.
- *Strength.*—Stems brittle.

Internode length: 1 to 4 cm.

FOLIAGE

Leaf:
- *Arrangement.*—Opposite.
- *Quantity.*—Approximately 6 leaves, in the 10-15 cm section from the top of the branch.
- *Average length.*—1.3 cm.
- *Average width.*—0.1 cm.
- *Shape of blade.*—Needle.
- *Apex.*—Acute.
- *Base.*—Attenuate.
- *Margin.*—Entire.
- *Texture of surfaces.*—All surfaces glabrous.
- *Pubescence.*—None.
- *Aspect.*—Straight, approximately 30 to 75 degree angle from stem.
- *Color.*—Young foliage: Near RHS Yellow-Green 147B. Mature foliage: Near RHS Green 137A.
- *Venation.*—Indistinguishable from foliage.
- *Petiole.*—Not present.

FLOWER

Natural flowering season: Plants planted during April through October in Kfar Hess, Israel begin flowering December through February, without a juvenility period. Plants flower continuously under short day conditions.

Days to flowering from rooted cutting: Short day photoperiodic conditions. No juvenility.

Inflorescence type: Panicle. Terminal and axillary occurring flowers.

Individual flower type: Single, 5 petals with hypanthium.

Persistent or self-cleaning: Self-Cleaning.

Rate of flower opening: 70 to 80 days from bud to fully opened flower.

Typical flowering stems harvested per plant: 120-150.

Flowering stem length: Average range between 60 to 80 cm.

Vase life of flowers: Two weeks.

Bud:
- *Shape.*—Round.
- *Length.*—0.35 cm.
- *Diameter.*—0.35 cm.
- *Texture.*—Glabrous.
- *Color.*—Near Red-Purple 65D.

Inflorescence size:
- *Diameter.*—Average 15 cm.
- *Length.*—Average 12 cm.

Flower size:
- *Diameter.*—1.2 cm.
- *Length.*—0.7 cm.

Corolla:
- *Flower longevity.*—Approximately 10 days.
- *Flower habit.*—Outwardly facing.
- *Flower shape.*—Obcanical hypanthium topped with 5 rotate non-overlapping petals.

Petals:
- *Length.*—0.4 cm.
- *Diameter.*—0.3 cm.
- *Quantity.*—5.
- *Texture.*—Smooth, upper and lower surfaces.
- *Apex.*—Obtuse rounded.
- *Base.*—Fused into a hypanthium.
- *Color.*—When opening: Upper surface: Near Red-purple 62D. Lower surface: Near Red-purple 69D. Fully opened: Upper surface: Near Red-purple 65D. Lower surface: Near Red-purple 65D. Aging: Upper surface: Near Red-purple 65D. Lower surface: Near Red-purple 65D.

Hypanthium:
- *Shape.*—Obconical.
- *Diameter.*—0.6 cm.
- *Length.*—0.2 cm.
- *Color.*—When opening: Upper surface: Near Greyed-Purple 187B. Lower surface: Near Red-purple 65D. Fully opened: Upper surface: Near Greyed-Purple 187B. Lower surface: Near Red-purple 65D. Aging: Upper surface: Near Greyed-Purple 187B. Lower surface: Near Red-purple 65D.

Calyx/sepals:
- *Quantity per flower.*—Single conical structure.
- *Shape.*—Conic.
- *Length.*—0.2 cm.
- *Width.*—0.6 cm.

*Margin*.—Entire incised approximately 1 mm.
*Texture*.—Smooth, upper and lower surfaces.
*Color*.—Upper surface: Near Green 137D. Lower surface: Near Green 137A.

Peduncle: Peduncle is the lateral branch.

Pedicel:
*Length*.—0.6 cm.
*Diameter*.—0.1 cm.
*Color*.—RHS.

Fragrance: None.

REPRODUCTIVE ORGANS

Stamens:
*Number*.—10.
*Filament length*.—1 mm.
*Filament color*.—Near RHS Yellow-Orange 16D.

Anthers:
*Shape*.—Oval.
*Length*.—0.25-0.5 mm.
*Width*.—Approximately 0.1 mm.
*Color*.—Near Greyed-purple 187B.

Pollen: Not observed.

Pistil:
*Number*.—1.
*Length*.—0.45 cm.
*Style*.—Length: 0.44 cm. Color: Near Red-Purple 65D.
*Stigma*.—Shape: Round. Color: Near Red-Purple 65D.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with RHS chart.

Disease/pest resistance: Neither resistance nor susceptibility to the normal diseases and pests of *Chamelaucium* have been observed to date.

Temperature tolerance: from −2° C. to 35° C.

Drought tolerance: Very good tolerance for drought.

What is claimed is:

1. A new and distinct cultivar of *Chamelaucium* plant named 'TITAN' as herein illustrated and described.

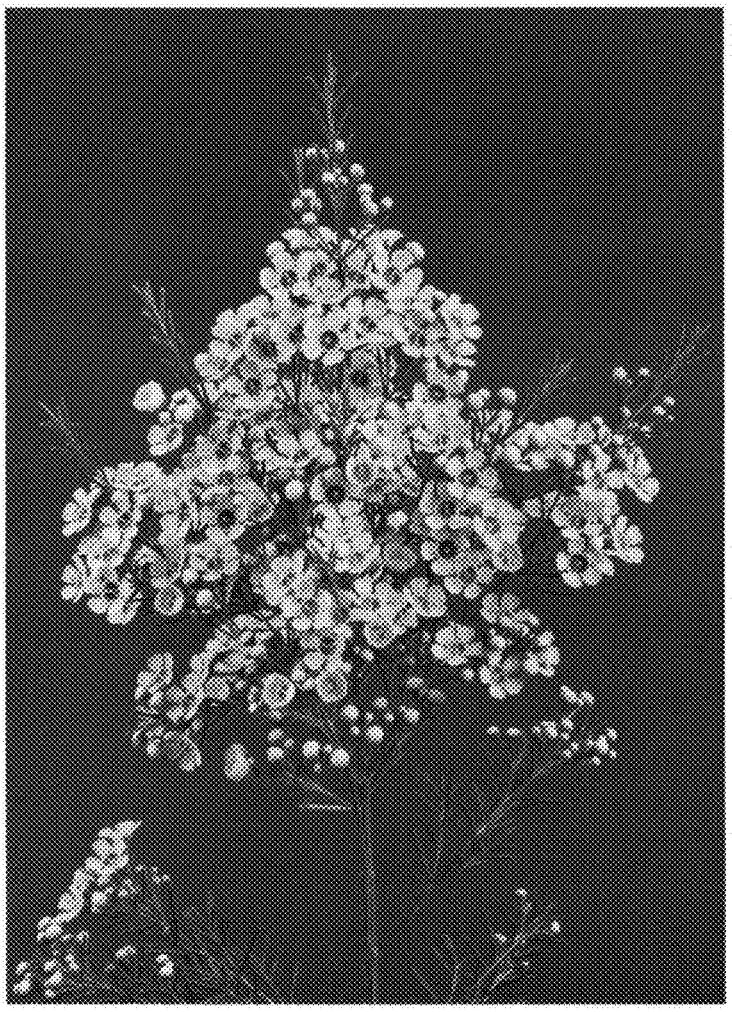

* * * * *